United States Patent [19]

Hirsch

[11] Patent Number: 5,265,655
[45] Date of Patent: Nov. 30, 1993

[54] DEVICE FOR MOVING A CUP HOLDER WITHIN AN ANALYZER

[75] Inventor: Alexander Hirsch, Stuttgart, Fed. Rep. of Germany

[73] Assignee: Eastman Kodak Company, Rochester, N.Y.

[21] Appl. No.: 732,274

[22] Filed: Jul. 18, 1991

[30] Foreign Application Priority Data

Jul. 20, 1990 [DE] Fed. Rep. of Germany ....... 4023144

[51] Int. Cl.$^5$ ................................ B65B 43/42
[52] U.S. Cl. .................. 141/130; 141/129; 141/180
[58] Field of Search ............ 141/129, 130, 131, 180, 141/155, 156, 157, 159, 167, 168, 174; 198/459, 463.4

[56] References Cited

U.S. PATENT DOCUMENTS

| | | | |
|---|---|---|---|
| 1,825,751 | 10/1931 | Meyer et al. | 141/168 |
| 2,239,710 | 4/1941 | Gordon | 198/460 |
| 3,503,265 | 3/1970 | Isreeli | 73/864.25 |
| 3,519,108 | 7/1970 | Webb et al. | 141/129 |
| 3,902,587 | 9/1975 | Checcucci | 198/419.3 |
| 4,194,613 | 3/1980 | Takano | 198/419.1 |
| 4,269,298 | 5/1981 | Mergl | 198/341 |
| 4,454,939 | 6/1984 | Kampf | 198/346.1 |
| 4,699,767 | 10/1987 | Aihara | 141/130 |

Primary Examiner—Henry J. Recla
Assistant Examiner—David J. Walczak
Attorney, Agent, or Firm—Dana M. Schmidt

[57] ABSTRACT

A device is disclosed for translatorily moving a plate-shaped cup holder, equipped with cups arranged successively in the direction of movement for receiving liquid, to the processing station of an analyzer. The cups are used for mixing viscous body fluid, e.g. blood, with a diluent.

Movement of the cup holder and exact positioning of the cups in the processing station are effected in that the cup holder frictionally rests on a driven endless belt, in that an incrementally driven indexing wheel is brought into engagement with the cups, and in that a sensor is arranged for detecting the passage of each cup and determining the indexing position of the indexing wheel in which a cup is located in its processing position.

6 Claims, 3 Drawing Sheets

DEVICE FOR MOVING A CUP HOLDER WITHIN AN ANALYZER

FIELD OF THE INVENTION

The present invention relates to a device for translatorily moving a plate-shaped cup holder, equipped with cups arranged successively in the direction of movement for receiving liquid, to the processing station of an analyzer.

BACKGROUND OF THE INVENTION

DE-PS 16 73 107 discloses an apparatus for analyzing liquids in which the sample tubes are moved by means of a chain drive within the analyzer. For this purpose, the individual chain links are provided with holding means into which the sample tubes can be inserted. The chain extends between two sprokets. The axle of one of the sprockets carries a disk having four recesses that are uniformly distributed over its periphery. In order to move a sample tube from a first processing station to a second, the disk rotates through 90 degrees and thereby carries along a sample tube engaged by a recess.

The known apparatus is very complex, space-consuming and requires regular maintenance if it is to operate reliably.

SUMMARY OF THE INVENTION

It is an advantageous feature of the present invention to provide a device of the generic type which is simply designed, operates reliably and guarantees exact positioning of the individual cups in a processing station.

It is a further advantageous feature to provide such a device that will move cups into a starting position on a continuously advancing member, and then index them alternately in parallel to, that is, with the direction of the advancing member, and then in opposition to the direction of the advancing member.

According to the invention, the above object is attained by a device for translatorily moving a liquid holder equipped with cups arranged successively in the direction of movement, to a processing station of an analyzer and aligning it in the station, comprising:

a driven continuous movement means on which a holder is placed, indexing means for providing relative motion on the continuous movement means that alternates between being opposite to the movement of the continuous movement means, and parallel to the movement, and a sensor means arranged in the area of the indexing means for detecting the passage of a cup controlled by the indexing means.

Preferably, the cup holder frictionally rests on a driven continuous movement means, an incrementally driven indexing wheel is brought into direct engagement with the cups and in that a sensor means is arranged in the area of the indexing wheel, detecting the passage of a cup and determining the indexing position of the indexing wheel in which a cup is located in its processing position.

Using simple means, the cups can thus be continuously fed to a processing station independent of the position of the continuous movement means. The exact alignment of the cups fed into the processing station is assured by means of the indexing wheel driven by a stepping motor in cooperation with the sensor means.

In a preferred embodiment the indexing wheel is designed as a gear with the shape and size of its tooth spaces being dimensioned such that they can directly engage the appropriately formed cups. This enables a reliable translatory movement and exact positioning of the cup holders without using additional gear elements.

Other features of the invention disclose that the central axis of the cup holder rests on the continuous movement means and that beneath and parallel thereto a housing bottom is provided at a distance slightly larger than the distance from the support surface of the cup holder to the lower end of a cup. Such configuration requires only a single continuous movement means since the cup bottoms are supported by the housing bottom and the cup holder is thus retained in a horizontal position.

Further features and advantages will be apparent from the description of an embodiment shown in the drawing and from the sub-claims.

DESCRIPTION OF THE PREFERRED EMBODIMENT

Figure 1:
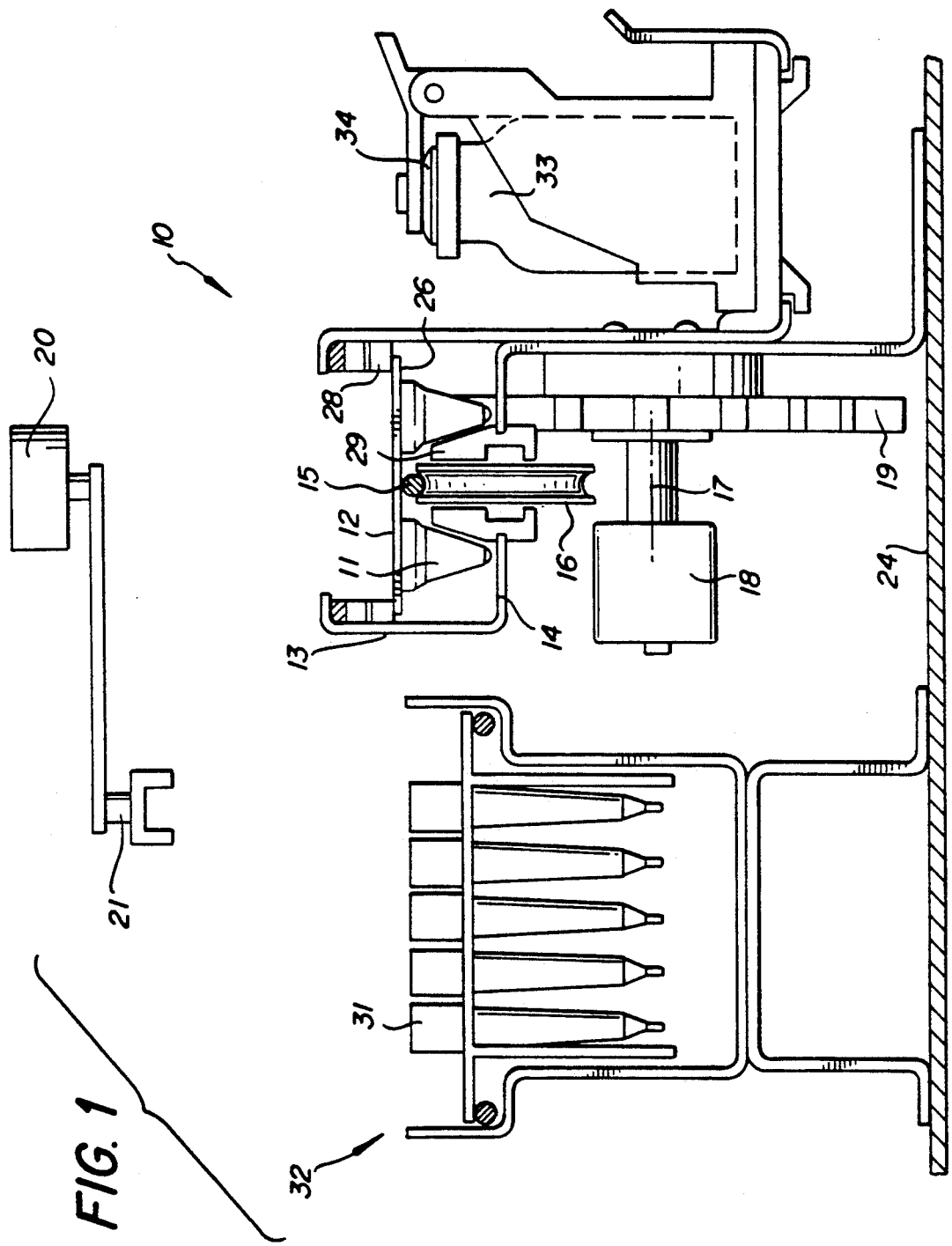
FIG. 1 shows a schematic representation of the arrangement of the device according to the invention within an analyzer.
Figure 2:
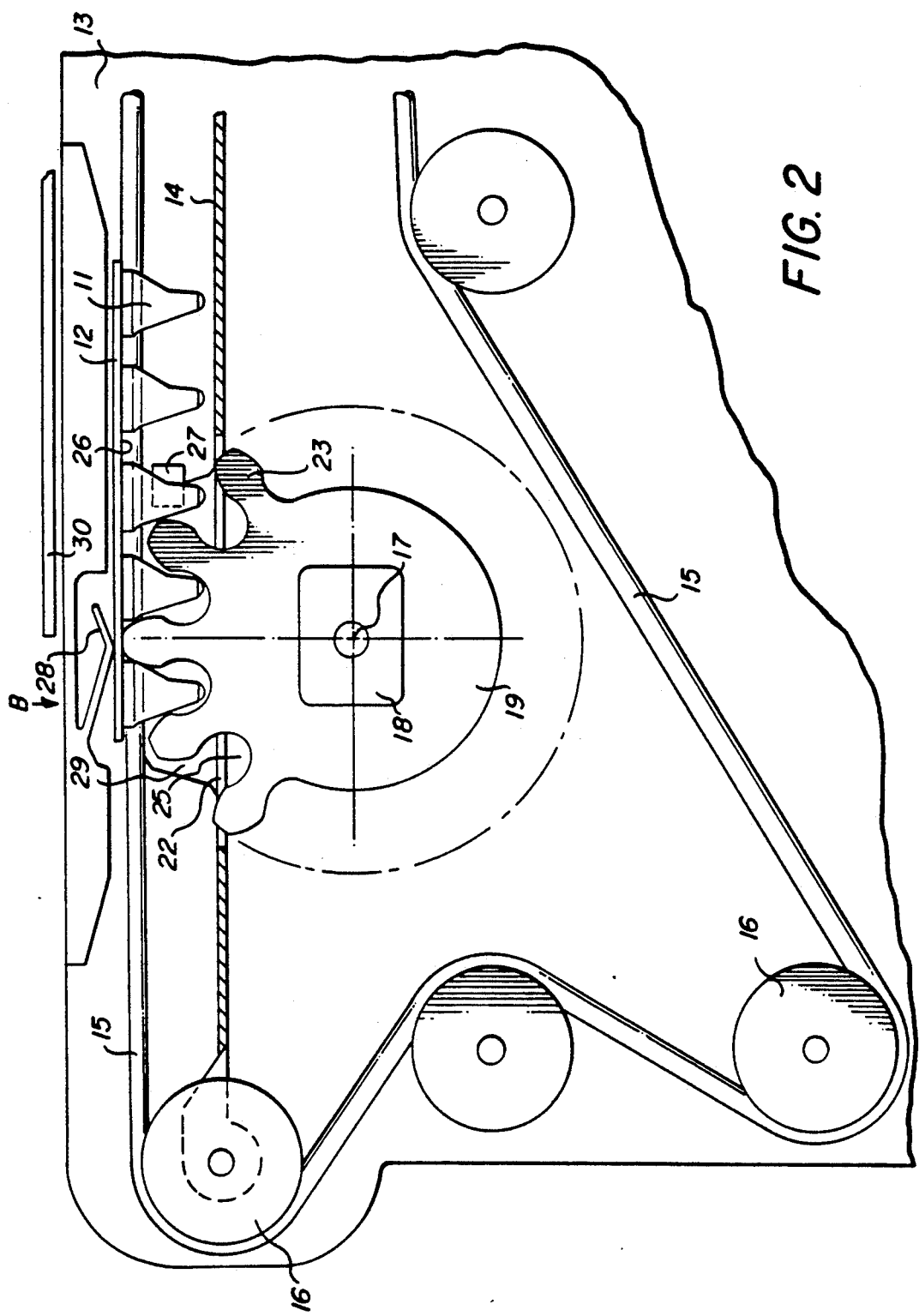
FIG. 2 is a side elevation in cross-section of the device according to FIG. 1 (enlarged representation)
Figure 3:
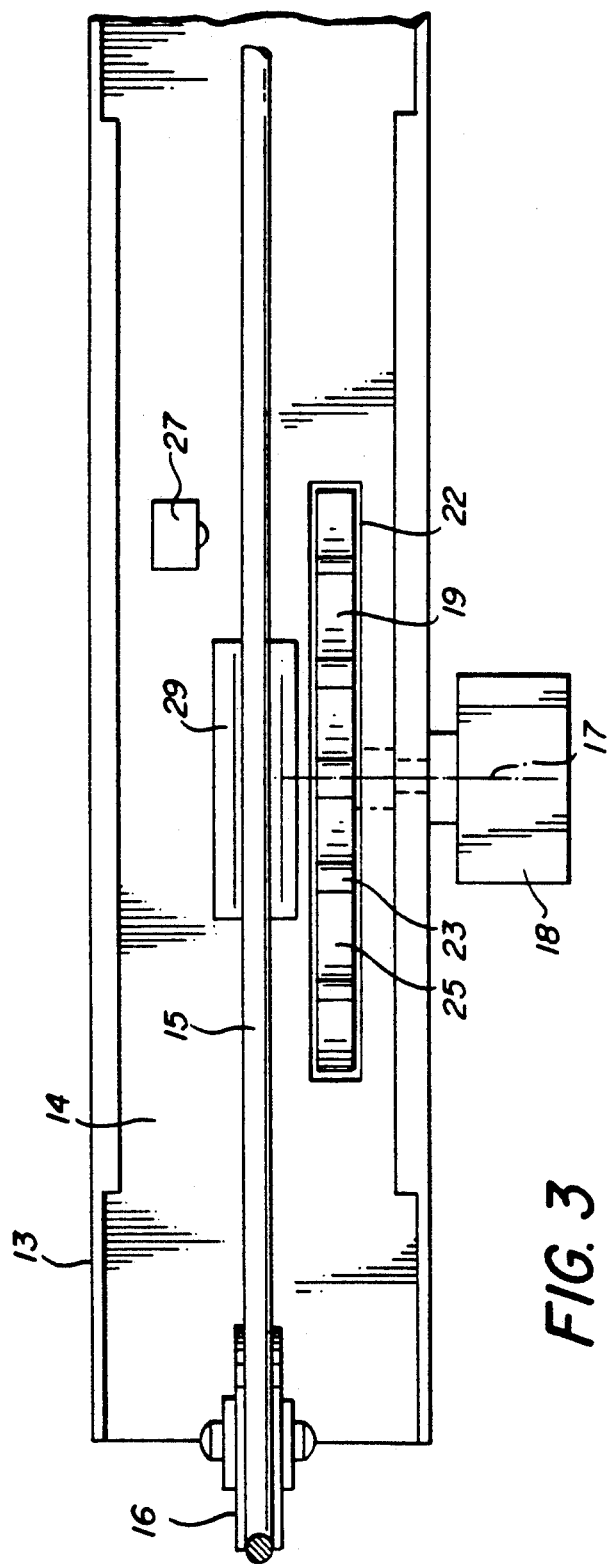
FIG. 3 is a top view of the device according to FIG. 1.
Figure 4:
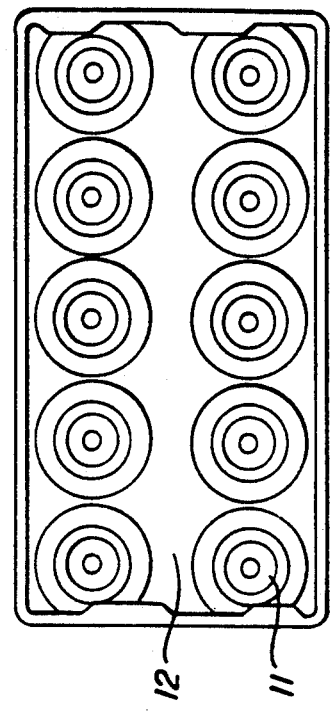
FIG. 4 shows a top view of the cup holder according to FIG. 2.

When examining body fluids, as for example blood serum, in an analyzer, it may happen that a liquid to be examined is too viscous and must be diluted in order to be able to obtain correct and usable results. For this purpose, cups 11 are provided in which the blood can be mixed with an appropriate diluent so as to obtain the required consistency. The present invention describes the feeding procedure of such cups to an analyzer and the alignment of same in a processing station.

In the embodiment shown in the drawing the cups 11 are arranged in pairs side by side in a cup holder 12 which is integral with the cups 11 and consists of a chemically resistant plastic material.

The device 10 is substantially comprised of an elongate housing 13 of U-shaped cross-section having a bottom 14, said housing being connected to a wall of the analyzer. Along the centerline of the elongate housing extends a continuous movement means designed as a belt 15 of circular cross-section which is tensioned and guided by several pulleys 16.

An indexing wheel 19 rotated about a shaft 17 and driven by a stepping motor 18 is aligned with a processing station B and arranged such that in the area of a recess 22 its indexing teeth extend through the housing bottom 14 and project therefrom. The indexing wheel 19 is thereby located in the vertical plane of a row of the successively arranged cups 11.

The indexing teeth 23 and the tooth spaces 25 are shaped such that they move directly into gear engagement with the cups 11 formed accordingly. The cup holder 12 virtually forms a rack cooperating with the indexing wheel 19. The distance between the support surface 26 of the cup holder 12 on belt 15 and the lower end portions of the cups 11 is slightly smaller than the spacing between the upper edge of belt 15 and the housing bottom 14.

In this way, the cup holder is held in a horizontal position. The passage of cups 11 and the exact indexing position of indexing wheel 19 is detected by a sensor means 27 arranged in the area of the indexing wheel 19. Alternately, sensor means 27 can be positioned to detect only the passage of a cup. Preferably, the sensor is an optoelectric sensor of a known type, and it senses both the leading edge of a cup and of the teeth of wheel 19.

For stabilizing the position of cup holder 12 when a cup 11 is located in the processing station B, spring elements 28 are provided at the side walls of housing 13 which press the cup holder 12 onto a block 29 with belt 15 being located in between.

In order to guarantee an unobstructed passage of the cup holders 12, the housing bottom 14 and the indexing wheel 19 are arranged such that the indexing teeth 23 which are not engaged with the cups 11 are positioned in or below the plane of housing bottom 14 when the indexing wheel 19 is in its indexing position.

During a mixing or diluting procedure, the analyzer operates as follows:

The continuous movement means designed as a belt 15 is driven by a motor (not illustrated). A cup holder 12 inserted in the analyzer rests on belt 15 and is frictionally advanced until the sensor means 27 detects the passage of the first cup 11. Thereupon, the stepping motor 18 is switched on and the indexing wheel 19 is rotated. The drive mechanism of belt 15 can now be turned off since one of the indexing teeth engages with the first cup 11 and advances it by one step corresponding to the pitch defined by the distance of two successive cups. Now the first pair of cups is positioned beneath a cover 30 protecting the cups from fouling by possible liquid splashes in the analyzer.

If the drive mechanism of belt 15 continues to operate, further cup holders 12 can be placed on belt 15 and advanced until they abut the cup holder positioned in front of them. Due to a mere frictional engagement with the belt, the cup holders remain in their standby positions.

If a blood sample needs to be diluted prior to analysis, this will be signalled and the cup holder 12 is advanced by the indexing wheel 19 until the first pair of cups is positioned in first processing station B. Aspirator 20 picks up a pipette 31 from a pipette tray 32 and collects a certain amount of blood from a sample tube (not illustrated) which is delivered into a cup 11. The used pipette 31 is discarded and a second one is picked up by the aspirator 20 from pipette tray 32. Now the aspirator 20 directs the fresh pipette 31 to a liquid container 33 whose lid 34 was previously automatically opened, aspirates a predetermined amount of liquid by means of a proboscis 21 and delivers it to cup 11 which is filled with blood and mixes it with the blood. As soon as blood and diluent have been mixed, the diluted blood mixture is re-aspirated and delivered to the analyzer for blood analysis.

When this procedure is terminated, the stepping motor 18 is turned on again and the cup holder 12 is moved back by one step so that the still non-used cup 11 is again moved under the protective cover 30. If both cups 11 of a pair of cups have been used, the cup holder 12 remains in its position and, if required, the cup holder is advanced to its next clean pair of cups.

When all cups 11 of a cup holder 12 are used up, the cup holder 12 is further advanced by belt 15 until it drops into a waste bin over the outermost pulley 16.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. A device for translatorily moving a liquid holder equipped with cups arranged successively in the direction of movement, to a processing station of an analyzer and aligning it in said station, comprising:
    a driven continuous movement means on which a holder is placed,
    indexing means for providing the holder with motion relative to said continuous movement means wherein the motion alternates between being opposite to the movement of said continuous movement means, and parallel to said movement, and
    a sensor means arranged on the device in the area of the indexing means for detecting the passage of a cup controlled by the indexing means and for controlling said indexing means in response to the passage of a cup.

2. A device according to claim 1, wherein said indexing means comprises a gear wheel having teeth shaped and sized to receive a cup portion of a holder.

3. A device according to claim 2, wherein said sensor means detects the passage of the cup holder by sensing the leading edge of a cup, and to align the indexing means in a position in which a cup is present in a processing position, the sensor means senses the leading edge of an indexing tooth of said indexing means.

4. A device according to claim 1, wherein the sensor means is an optoelectric sensor.

5. A device according to claim 1, wherein the continuous movement means is a belt of circular cross-section.

6. A device according to claim 1, wherein the cup holder and the cups are a molded plastic member.

* * * * *